United States Patent [19]

Murguet et al.

[11] Patent Number: 4,484,365

[45] Date of Patent: Nov. 27, 1984

[54] FLAP-TYPE PROSTHETIC HEART VALVE

[76] Inventors: Robert F. Murguet, 4 rue de Constantine, Lyon 1; Joelle M. J. Lugarini-Tardy, 11 Residence du Val, Palaiseau, Essone, both of France

[21] Appl. No.: 438,287

[22] Filed: Nov. 1, 1982

[30] Foreign Application Priority Data

Nov. 5, 1981 [FR] France ............................... 81 20898

[51] Int. Cl.³ .............................................. A61F 1/22
[52] U.S. Cl. ...................................... 3/1.5; 137/512.1; 137/527
[58] Field of Search .................. 3/1.5; 137/512.1, 527, 137/527.8

[56] References Cited

U.S. PATENT DOCUMENTS 3,476,143 11/1969 Kaster ................................... 3/1.5 X
4,078,268 3/1978 Possis ....................................... 3/1.5
4,363,142 12/1982 Meyer ...................................... 3/1.5

FOREIGN PATENT DOCUMENTS 7906506 3/1981 Netherlands ............................ 3/1.5
843976 7/1981 U.S.S.R. .................................. 3/1.5

Primary Examiner—Ronald L. Frinks
Attorney, Agent, or Firm—Karl F. Ross

[57] ABSTRACT

A prosthetic cardiac valve comprises a collar adapted to be secured in a blood-flow passage, a pair of pivots in the collar extending generally parallel to each other and spaced apart perpendicularly to the direction of flow through the passage, and respective flaps carried on the pivots and having inner edges. The flaps are pivotal on the respective pivots between closed positions transverse to and blocking the passage with the inner edges touching and lying between the respective pivot axes and open positions extending generally parallel to the flow direction downstream from the respective pivots. One of the flaps is constructed so that when closed it diverts flow in the passage at the other flap to move same into the open position. One of the pivot axes is downstream of the other axis and the respective flap is of substantially greater surface area than the other flap.

9 Claims, 16 Drawing Figures

FLAP-TYPE PROSTHETIC HEART VALVE

FIELD OF THE INVENTION

The present invention relates to a prosthetic heart valve. More particularly this invention concerns a replacement mitral or aortal valve.

BACKGROUND OF THE INVENTION

Prosthetic cardiac valves can be surgically implanted to replace the main heart valves, that is the mitral and aortal valves. Such valves must open and close rapidly while imparting minimal turbulence to blood flow in the passage in which they are provided. Obviously if they are difficult to open they will increase upstream blood pressure and the load on the heart, and if they do not close fully they will allow perilous backflow. In addition if they create excessive turbulence they can cause life-threatening embolisms.

It is known to make such valves of animal tissue, neutralized to prevent rejection. Such valves can exactly mimic the action of the valves they replace, but are prone to physical breakdown and mechanical failure. Thus on the one hand there is the advantage of little increase in the likelihood of embolism, thereby eliminating anticoagulant treatment, but on the other their potentially short service life poses a constant danger for the host.

Recourse is therefore normally had to sturdier mechanical valves. A standard type comprises a cage having at one end a seat and containing a ball that can move against the seat or from it, depending on the flow direction. Such an arrangement has a service life that can be expected to last the lifetime of the host, but normally creates quite some turbulence in the blood flow it controls. To prevent thrombosis it is therefore necessary for the host to be maintained on a treatment of anticoagulants.

It is also known to use a standard flap- or disk-type check valve mounted in a collar that is sewn into the passage. The flap opens by moving into a position parallel to the flow, and closes by moving into a position across the flow and blocking the collar. Even when such a valve is equipped with two flaps to open as quickly as possible, it creates considerable turbulence just as it starts to open, normally in the first 10° of pivoting. Thus thrombosis, embolisms, and hemolytic degradations are a problem.

OBJECTS OF THE INVENTION

It is therefore an object of the present invention to provide an improved replacement heart valve.

Another object is the provision of such a replacement heart valve which overcomes the above-given disadvantages.

A further object is to provide such a valve which opens so quickly that it creates no appreciable turbulence in the blood flow through it.

SUMMARY OF THE INVENTION

These objects are attained according to the instant invention in a prosthetic cardiac valve comprising a collar adapted to be secured in a blood-flow passage, a pair of pivots in the collar extending generally parallel to each other and spaced apart perpendicularly to the direction of flow through the passage, and respective flaps carried on the pivots and having inner edges. The flaps are pivotal on the respective pivots between closed positions transverse to and blocking the passage with the inner edges touching and lying between the respective pivot axes and open positions extending generally parallel to the flow direction downstream from the respective pivots. One of the flaps is constructed so that when closed it diverts flow in the passage at the other flap to move same into the open position.

Thus with the system of the invention the instantaneous pulse of turbulence that is created as the one flap opens is employed to open the other flap very rapidly, thereby shortening the opening movement and limiting turbulence enormously.

According to this invention one of the pivot axes is downstream of the other axis. Thus the flap with the upstream pivot will open first, creating the spurt that opens the other flap.

In accordance with another feature of the invention the one flap is of larger surface area than the other flap. Normally in such an arrangement the larger flap is the one with the upstream pivot, so the smaller flap with its correspondingly smaller inertia will be the one to be driven open by the flow from the larger one. As a pressure pulse strikes the first, larger flap it opens slightly, creating a turbulence that is effective to open the smaller flap very rapidly The inner edges of the flaps of this invention are formed as lips projecting generally downstream in the closed position. More particularly they are substantially part-cylindrical, centered on respective axes of curvature parallel to the respective pivot axes. In either case the inner edges according to this invention extend generally parallel to the respective axes. When closed the pressure will hold these lips tightly together, preventing backflow.

According to another feature of the invention the flaps are generally U-shaped in a direction perpendicular to the respective axes and lie generally against the collar in the open positions. The radius of curvature is generally equal to that of the collar, which in turn is of course the same as that of the passage in which it is mounted, so that when open the flaps lie virtually against the inside walls of the passage, almost totally out of the flow path of the blood in the passage.

In accordance with another feature of this invention the flaps have outer edges engageable with the collar and same is formed with a ridge lying downstream of and engaging the outer edges in the closed positions. The ridges lie mainly outside the pivot axes. Thus the flaps seat firmly when closed, with their outer edges lying on this ridge and their inner edges snugly abutting each other.

DESCRIPTION OF THE DRAWING

The above and other features and advantages will become more readily apparent from the following, reference being made to the accompanying drawing in which.

SPECIFIC DESCRIPTION

Figure 1:
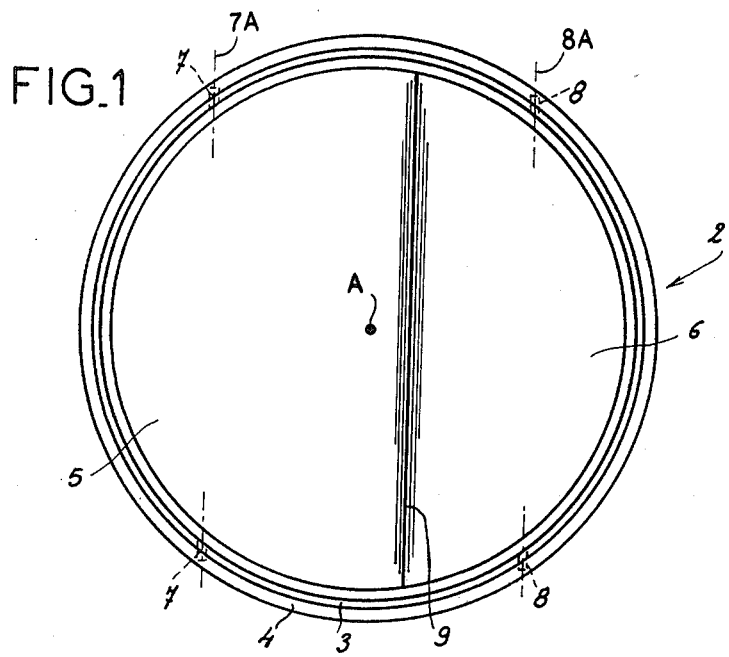
FIG. 1 is a top view of a valve according to the invention in the fully closed position.
Figure 2:
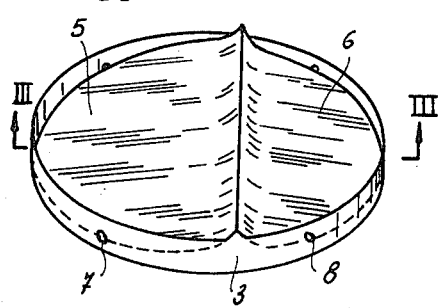
FIG. 2 is a perspective view of the valve according to the invention in the fully closed position.
Figure 7:
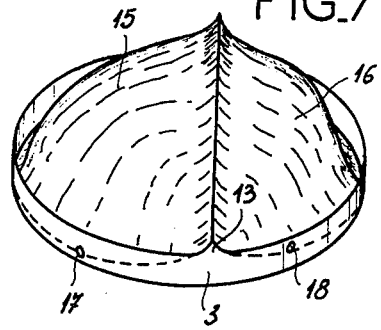
FIGS. 7 through 11 are views corresponding respectively to FIGS. 2 through 6 of another valve according to this invention.
Figure 3:
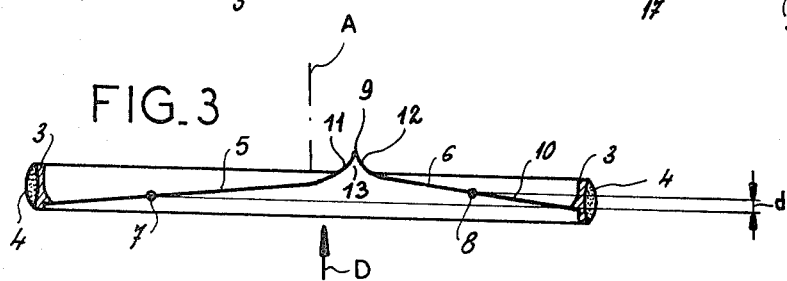
FIG. 3 is a large-scale section taken along line III—III of FIG. 2.
Figure 8:
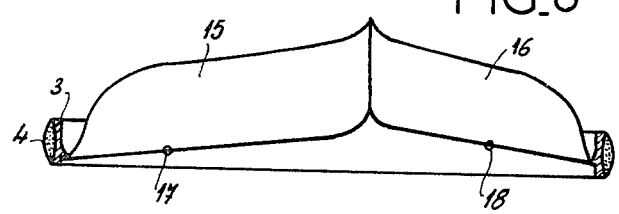
Figure 4:
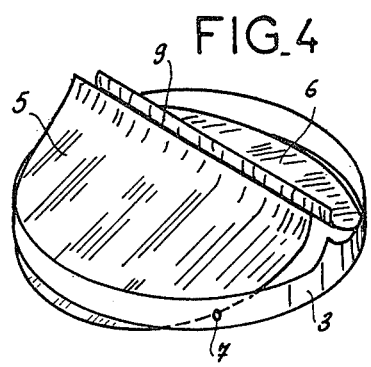
FIG. 4 is a perspective view showing the valve partly open.
Figure 9:
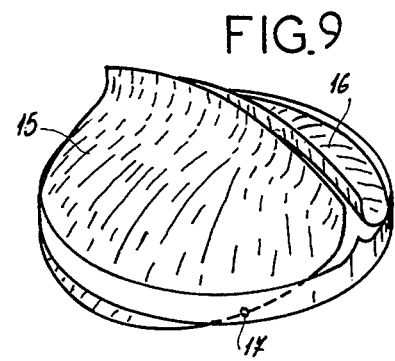
Figure 5:
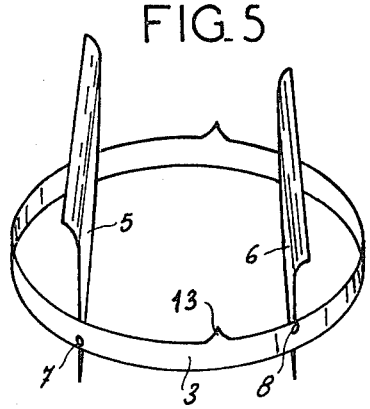
FIG. 5 is a perspective view showing the valve fully open.
Figure 10:
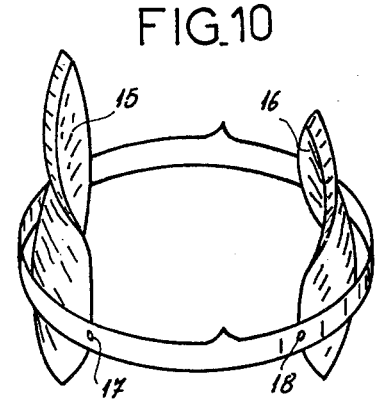
Figure 6:
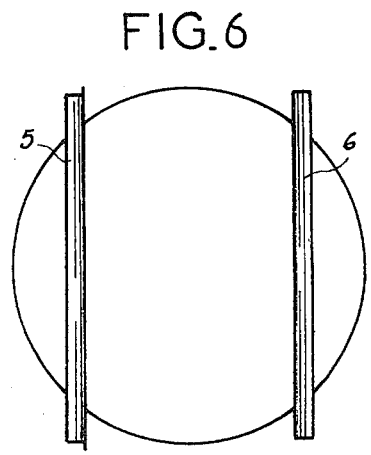
FIG. 6 is a top view of the valve in the fully open position.
Figure 15:
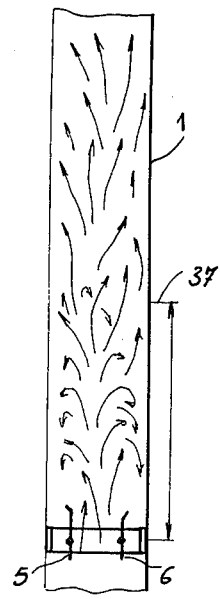
FIGS. 15 and 16 are views like FIG. 14 showing the valves of FIGS. 1-6 and 7-11, respectively.

As seen in FIGS. 1-6 a replacement cardiac valve 2 according to this invention has a rigid cylindrical collar 3 centered on an axis A and provided externally with a polytetrafluorethylene ring 4 by means of which it is mounted in a passage 1 shown diagrammatically in FIG. 15, which passage 1 can extend between ventricles of a heart or be in the aorta. Two similar flaps 5 and 6 that together can completely block the collar 3 are mounted by respective pivots 7 and 8 defining respective axes 7A and 8A on the collar 3. These flaps 5 and 6 have respective part-cylindrical inner edges or lips 11 and 12 that meet at a straight line 9 parallel to the axes 7A and 8A, which themselves are much closer to the outer edges of the respective flaps 5 and 6 than to the inner edges 11 and 12. Outside the axes 7A and 8A the ring 3 is formed with a ridge forming a shoulder directed upstream and against which the outer edges of the flaps 5 and 6 lie when in the closed position of FIGS. 1-3. At the line 9 the ring 3 further has two small points or cusps 13 which fit at the line 9 between the lips 11 and 12 in the closed position As illustrated in FIG. 3 the two pivots 7 and 8, and of course their respective axes 7A and 8A, are offset by a small distance d relative to the axis A, which itself is parallel to the flow direction D through the valve 2. Thus a pulse of blood will strike the flap 5 slightly before and with slightly greater force than the flap 6.

In addition the flap 5 is of substantially greater surface area than the flap 6, so that the line 9 is closer to the axis 8A than to the axis 7A. In this arrangement the ring or collar 3 has a diameter of 32 mm, and the overall diameter of the plates 5 and 6 is 29 mm. The flap 5 is some 10% to 15% larger than the flap 6 in surface area, so its diametral dimension perpendicular to the line 9 is some 16.24 mm and that of the flap 6 is 12.76 mm. The distance d is 2.5 mm and the curved regions 11 and 12 extend some 6 mm perpendicular to the line 9 in the plane of the valve.

When a pressure pulse arrives at the valve 2 according to this invention it will first strike the larger surface of the upstream flap 5, opening it slightly. This will cause an instant of turbulence that will swing the other smaller flap 6 open with great speed, moving it into the position of FIGS. 5 and 6.

Figure 14:
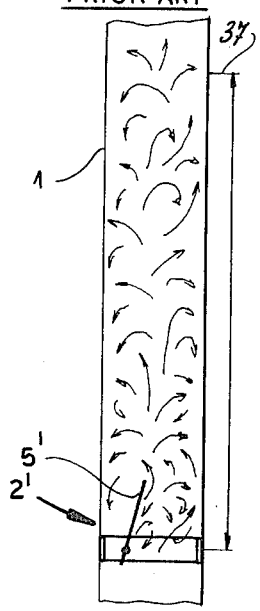
FIG. 14 is a largely schematic view illustrating a prior-art valve.

In a standard prior-art valve 2' having a single flap 5' as seen in FIG. 14 a turbulent zone 37 having a length equal to 4 to 5 times its diameter is formed immediately downstream of the valve 2'. Obviously such turbulence creates a thrombosis-embolism risk.

With the valve 2 according to this invention a tubulent zone 37 is created which is about half as long. Thus the need to treat the person in whom this valve 2 is implanted with anticoagulants is reduced or even eliminated.

Figure 11:
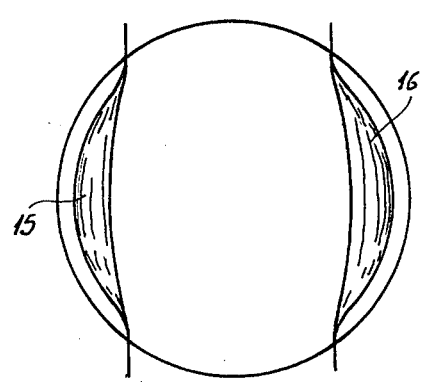

FIGS. 7-11 show another valve according to this invention having a pair of flaps 15 and 16 pivoted on axes 17 and 18. The position of the axes 17 and 18 is substantially identical to that of the axes 7 and 8 relative to the flow direction. In this arrangement, however, the flaps 15 and 16 are generally U-shaped so that, as best seen in FIG. 11, they lie substantially against the walls of the passage when fully open. This type of structure is particularly useful in places with good clearance, as in an aorta. As a result parasitic flows will be largely eliminated.

Figure 16:
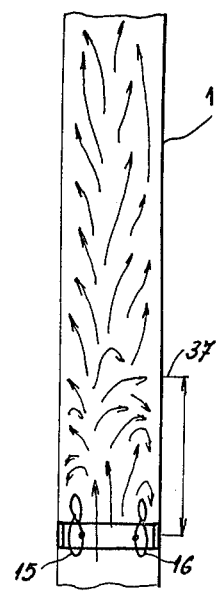

In fact as shown in FIG. 16 this type of structure will reduce the turbulent zone 37 to well below half of the size of the zone 37 of the prior-art arrangement and even to less than that of the valve 2.

Figure 12:
FIGS. 12 and 13 are views like FIGS. 3 and 8 showing two other valves according to the invention.

FIG. 12 shows flaps 25 and 26 which are cylindrically curved over their entire surfaces. The opening and closing action of such a valve is very smooth.

Figure 13:
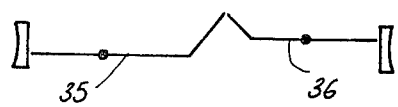

In addition in FIG. 13 the flaps 35 and 36 are formed entirely of flat sections. The instant invention permits of several different types of construction. In any case the use of lips extending downstream at the inner edges ensures smooth closing, minimal wear at this critical region, and a good seal when closed.

The valve according to the instant invention can in fact be counted on to operate virtually as smoothly as valves made of animal tissue and with as little turbulence, but can be counted on to last virtually indefinitely. They will effectively replace valves useless by congenital deformity or disease.

We claim:

1. A prosthetic cardiac valve comprising:
   a collar adapted to be secured in a blood-flow passage;
   a pair of pivots in the collar forming respective pivot axes extending generally parallel to each other and spaced apart perpendicularly to the direction of flow through the passage; and
   respective differently constructed flaps carried on the pivots and having inner edges, the flaps being pivotal on the respective pivots between closed positions transverse to and blocking the passage with the inner edges touching and lying between the respective pivot axes and open positions extending generally parallel to the flow direction downstream from the respective pivots, one of the flaps being constructed so that when moved by flow in the passage out of the closed position it diverts flow in the passage at the other flap to move same into the open position.

2. The prosthetic cardiac valve defined in claim 1 wherein the inner edges are formed as lips projecting generally downstream in the closed position.

3. The prosthetic cardiac valve defined in claim 1 wherein the inner edges extend generally parallel to the respective axes.

4. The prosthetic cardiac valve defined in claim 1 wherein the flaps are generally U-shaped in a direction perpendicular to the respective axes and lie generally against the collar in the open positions.

5. The prosthetic cardiac valve defined in claim 1 wherein the flaps have outer edges engageable with the collar and same is formed with a ridge lying downstream of and engaging the outer edges in the closed positions.

6. The prosthetic cardiac valve defined in claim 5 wherein the ridges lie mainly outside the pivot axes.

7. A prosthetic cardiac valve comprising:

a collar adapted to be secured in a blood-flow passage;

a pair of pivots in the collar forming respective pivot axes extending generally parallel to each other and spaced apart perpendicularly to the direction of flow through the passage; and respective flaps carried on the pivots and having inner edges, the flaps being pivotal on the respective pivots between closed positions transverse to and blocking the passage with the inner edges touching and lying between the respective pivot axes and open positions extending generally parallel to the flow direction downstream from the respective pivots, one of the flaps being constructed so that when closed it diverts flow in the passage at the other flap to move same into the open position, one of the axes being downstream of the other axis.

8. A prosthetic cardiac valve comprising:

a collar adapted to be secured in a blood-flow passage;

a pair of pivots in the collar forming respective pivot axes extending generally parallel to each other and spaced apart perpendicularly to the direction of flow through the passage; and respective flaps carried on the pivots and having inner edges, the flaps being pivotal on the respective pivots between closed positions transverse to and blocking the passage with the inner edges touching and lying between the respective pivot axes and open positions extending generally parallel to the flow direction downstream from the respective pivots, one of the flaps being constructed so that when closed it diverts flow in the passage at the other flap to move same into the open position, the one flap being of larger surface area than the other flap.

9. A prosthetic cardiac valve comprising:

a collar adapted to be secured in a blood-flow passage;

a pair of pivots in the collar forming respective pivot axes extending generally parallel to each other and spaced apart perpendicularly to the direction of flow through the passage; and respective flaps carried on the pivots and having inner edges, the flaps being pivotal on the respective pivots between closed positions transverse to and blocking the passage with the inner edges touching and lying between the respective pivot axes and open positions extending generally parallel to the flow direction downstream from the respective pivots, one of the flaps being constructed so that when closed it diverts flow in the passage at the other flap to move same into the open position, one of the axes being downstream of the other axis and the respective flap being of larger surface area than the other flap.

* * * * *